(12) United States Patent
Hossain

(10) Patent No.: US 9,575,018 B2
(45) Date of Patent: Feb. 21, 2017

(54) SYSTEM AND METHOD FOR TESTING CERAMIC COATINGS

(71) Applicant: Cerium Laboratories, Austin, TX (US)

(72) Inventor: Timothy Hossain, Austin, TX (US)

(73) Assignee: CERIUM LABORATORIES, LLC, Austin, TX (US)

( * ) Notice: Subject to any disclaimer, the term of this patent is extended or adjusted under 35 U.S.C. 154(b) by 128 days.

(21) Appl. No.: 14/487,089

(22) Filed: Sep. 15, 2014

(65) Prior Publication Data

US 2015/0078517 A1    Mar. 19, 2015

Related U.S. Application Data

(60) Provisional application No. 61/878,550, filed on Sep. 16, 2013.

(51) Int. Cl.
*G01N 23/223* (2006.01)
*G01N 33/38* (2006.01)
*G01N 33/00* (2006.01)

(52) U.S. Cl.
CPC .......... *G01N 23/223* (2013.01); *G01N 33/388* (2013.01); *G01N 2033/0096* (2013.01)

(58) Field of Classification Search
CPC .................................................. G01N 23/223
USPC ...................................................... 378/44–50
See application file for complete search history.

(56) References Cited

U.S. PATENT DOCUMENTS

| | | | | |
|---|---|---|---|---|
| 4,169,228 A * | 9/1979 | Briska | ................. | G01N 23/223 378/45 |
| 5,062,127 A * | 10/1991 | Sayama | ............... | G01N 23/223 378/207 |
| 5,457,726 A * | 10/1995 | Miyazaki | ............. | G01N 23/223 378/45 |
| 5,497,407 A * | 3/1996 | Komatsu | .............. | G01N 23/223 378/45 |
| 5,527,707 A * | 6/1996 | Fukazawa | ............ | G01N 23/223 250/492.2 |
| 5,636,256 A * | 6/1997 | Matumura | ........... | G01N 23/223 378/45 |
| 5,686,314 A * | 11/1997 | Miyazaki | ................ | G01N 1/40 134/902 |
| 5,732,120 A * | 3/1998 | Shoji | .................... | G01N 23/223 378/210 |
| 5,742,658 A * | 4/1998 | Tiffin | ..................... | G01N 23/20 257/E21.53 |
| 5,754,620 A * | 5/1998 | Hossain | ............... | G01N 23/223 378/44 |
| 5,778,039 A * | 7/1998 | Hossain | ........... | G01N 23/20008 378/44 |
| 5,866,899 A * | 2/1999 | Hossain | ................. | G01N 23/22 250/252.1 |
| 6,041,096 A * | 3/2000 | Doi | ..................... | G01N 23/223 378/45 |

(Continued)

*Primary Examiner* — Allen C. Ho

(57) ABSTRACT

A method of testing for impurities includes directing an x-ray source toward a surface at an angle α relative to the plane of the surface, the surface defined by a ceramic coating over a crystalline substrate; detecting x-ray fluorescent radiation emitted from the ceramic coating at an angle θ different from the angle α and its supplementary angle; and comparing characteristics of the detected x-ray fluorescent radiation to characteristics associated with impurities.

20 Claims, 2 Drawing Sheets

(56) References Cited

U.S. PATENT DOCUMENTS

| | | | | |
|---|---|---|---|---|
| 6,173,036 B1 * | 1/2001 | Hossain | ............... | G01N 23/223 |
| | | | | 378/45 |
| 6,292,532 B1 * | 9/2001 | Kawahara | ............ | G01N 23/223 |
| | | | | 378/45 |
| 7,649,975 B2 * | 1/2010 | Boyden | .................. | A61B 5/415 |
| | | | | 378/44 |
| 7,864,919 B1 * | 1/2011 | Eyre | .................... | G01N 23/223 |
| | | | | 378/44 |
| 8,093,136 B2 * | 1/2012 | Endo | ................ | H01L 21/76254 |
| | | | | 257/E21.561 |
| 8,130,903 B2 * | 3/2012 | Corbett | ................ | E21B 10/567 |
| | | | | 378/44 |
| 8,410,474 B2 * | 4/2013 | Okai | .................... | B82Y 40/00 |
| | | | | 257/29 |
| 8,471,237 B2 * | 6/2013 | Okai | .................. | H01L 21/2855 |
| | | | | 257/621 |
| 8,476,739 B2 * | 7/2013 | Okai | ....................... | C23C 16/26 |
| | | | | 257/29 |
| 8,513,603 B1 * | 8/2013 | Lederman | ............ | G01N 23/223 |
| | | | | 250/305 |
| 8,557,718 B2 * | 10/2013 | Vermang | ............ | H01L 31/1868 |
| | | | | 257/E21.214 |
| 8,697,541 B1 * | 4/2014 | Kumar | ............. | H01L 21/02381 |
| | | | | 257/103 |
| 9,006,083 B1 * | 4/2015 | Kumar | ............. | H01L 21/02381 |
| | | | | 257/190 |

\* cited by examiner

SYSTEM AND METHOD FOR TESTING CERAMIC COATINGS

CROSS-REFERENCE TO RELATED APPLICATION(S)

The present application claims benefit of and is a non-provisional of U.S. Provisional Patent Application No. 61/878,550, entitled "SYSTEM AND METHOD FOR TESTING CERAMIC COATINGS" filed on Sep. 16, 2013, the entirety of which is herein incorporated by reference.

FIELD OF THE DISCLOSURE

This disclosure, in general, relates to systems and methods for testing ceramic coatings.

BACKGROUND

In industries, such as the semiconductor, microfluidics, micro-electromechanical (MEMs), and optical industries, the quality of substrates and layers upon which or within which devices are constructed influences the performance of such devices. In particular, impurities within substrates or ceramic layers can influence the performance of the substrate or can leach into other device layers, influencing the functionality of other layers or influencing the performance of the device. As such, testing substrates and ceramic layers for impurities can improve process control and enhance device performance.

Conventional techniques for testing quality and composition of ceramic layers on substrates rely upon destructive testing. A sample from a batch of coated substrates is selected and subjected to destructive testing. From the results of the destructive testing, the quality and composition of the substrates and coatings of the remaining substrates is inferred. However, such testing reduces yields by destroying expensive substrate stock and may have limited use when dealing with ceramic coatings that are resistant to conventional destructive testing methods.

As such, an improved testing method would be desirable.

BRIEF DESCRIPTION OF THE DRAWINGS

The present disclosure may be better understood, and its numerous features and advantages made apparent to those skilled in the art by referencing the accompanying drawings.

The use of the same reference symbols in different drawings indicates similar or identical items.

DETAILED DESCRIPTION

In an exemplary embodiment, a method for testing a ceramic coating on a substrate includes directing an x-ray source at a surface of the ceramic coating and detecting fluorescence emanating from the coating. The fluorescence emanating from the coating can be indicative of impurities within the coating. Characteristics of the fluorescence, such as wavelength, frequency or energy, can be compared with characteristics of impurities. As such, impurities can be detected using such a method. In a further example, relative characteristics of impurities, such as peak height or counts, can be compared to relative characteristics of electromagnetic signals indicative of other components of the ceramic coating, and as a result, relative composition of the ceramic coating can be measured.

Figure 1:
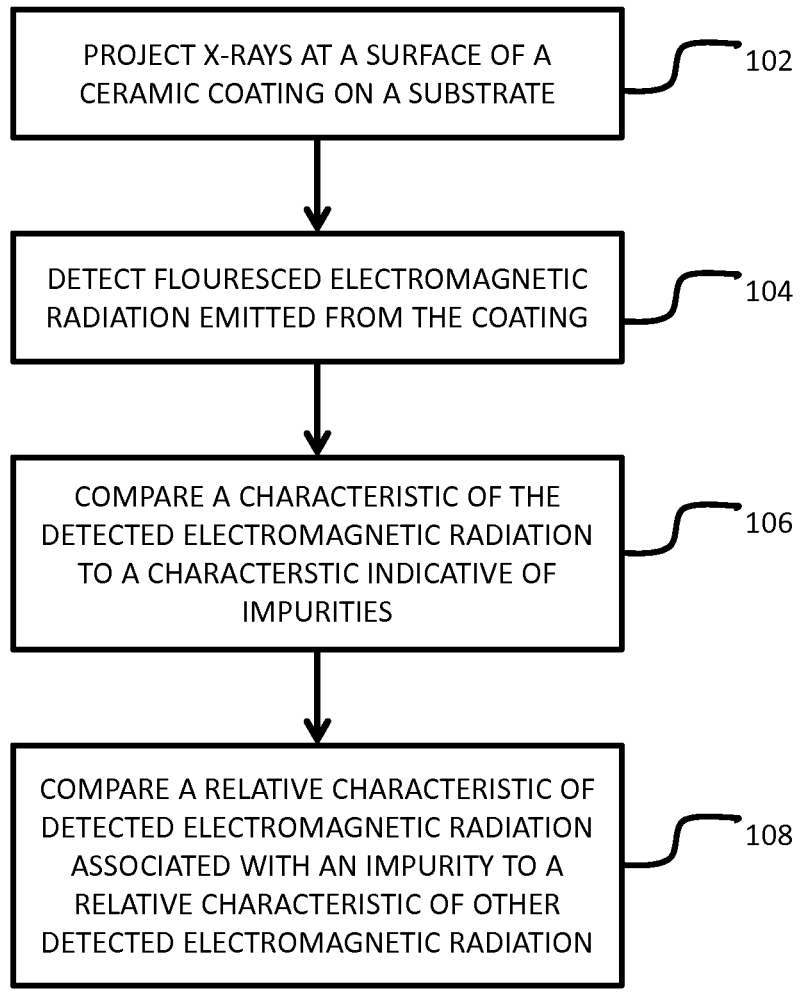
FIG. 1 includes a block flow diagram illustrating an exemplary method for testing a ceramic coated substrate.

FIG. 1 includes an illustration of an exemplary method for testing characteristics of a ceramic coating over a substrate. As illustrated at 102, x-rays can be projected from an x-ray source to a surface of the ceramic coating on the substrate. X-rays directed at the surface can have a wavelength in the range of 0.01 nm to 10 nm, such as a wavelength in the range of 0.1 nm to 1 nm. In a further example, the x-ray source may have an energy level in a range of 1 keV to 25 keV, such as a range of 2 keV to 21 keV. For example, the energy can be in a range of 2 keV to 5 keV. In another example, the energy can be in a range of 7 keV to 11 keV. In a further example, the energy can be in a range of 18 keV to 21 keV.

In a particular example, the ceramic coating is an amorphous ceramic coating or a polycrystalline ceramic coating. The substrate over which the coating is formed can be crystalline, such as monocrystalline. In particular, the crystalline substrate can be a monocrystalline silicon substrate. Applicants have discovered that when directing x-rays at a coating that is polycrystalline or amorphous and disposed over a crystalline substrate, the x-rays penetrate and migrate through the coating and reflect from a surface of the crystalline substrate.

Figure 2:
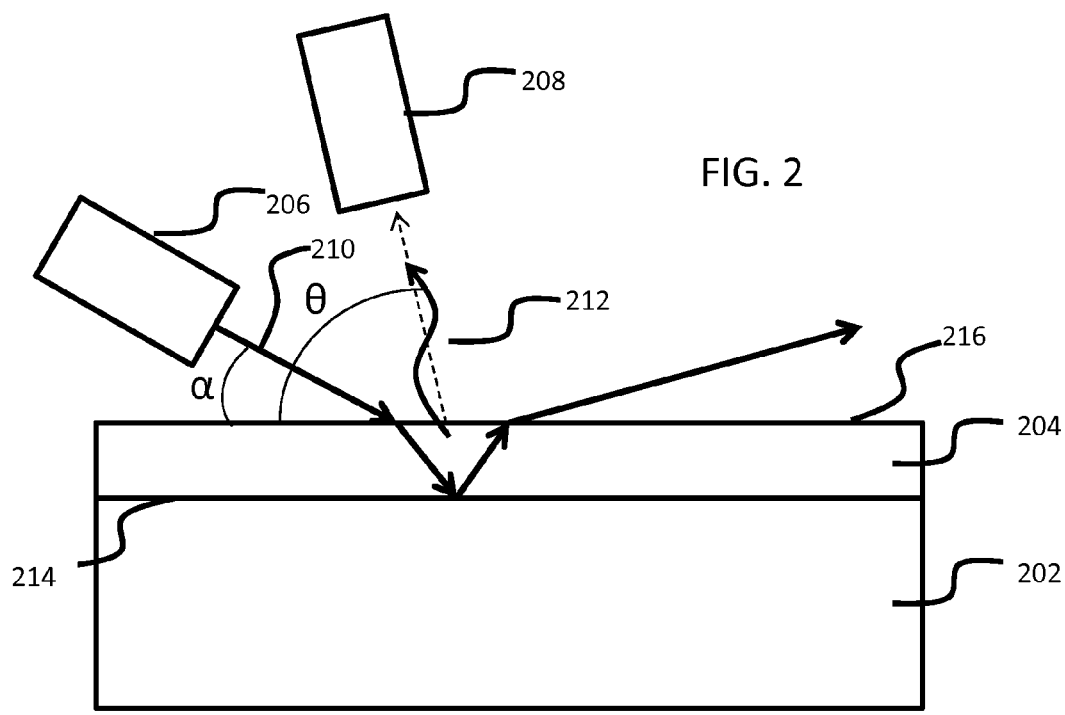
FIG. 2 includes an illustration of an exemplary system for testing a ceramic coating.

For example, as illustrated in FIG. 2, an x-ray source 206 is directed at a surface 216 of a ceramic coating 204 disposed over a crystalline substrate 202. The x-rays 210 can be directed at the surface 216 at an angle $\alpha$. In an example, the angle $\alpha$ is less than or equal to a critical angle. The critical angle is an angle at which total reflection would be expected if the x-ray 210 were directed at the crystalline surface 214 of the crystalline substrate 202. In particular, the angle $\alpha$ is not greater than 15° relative to the plane of the surface 216, such is not greater than 10°. The angle $\alpha$ can be in the range of 0.01° to 10°, such as a range of 0.015° to 5.0°, a range of 0.1° to 5.0°, or even range of 1.0° to 5.0°.

When the x-rays 210 impinge on the surface 216 of the ceramic coating 204, the x-rays 210 migrate to the crystalline surface 214, which forms an interface between the crystalline substrate 202 and the ceramic coating 204. At the crystalline surface 214, the x-rays 210 are reflected, penetrating not greater than, for example, 100 Å into the crystalline structure of the crystalline substrate 202 before being reflected back through the ceramic coating 204. As the x-rays 210 migrate through the bulk material of the ceramic coating 204, the x-rays can cause constituent atoms and impurities to fluoresce, emitting electromagnetic radiation indicative of the atom fluorescing.

Returning to FIG. 1, as illustrated at 104, electromagnetic radiation emitted from constituent atoms and impurities of the ceramic coating 204 can be detected. As illustrated in FIG. 2, as the x-rays 210 migrate through the ceramic coating 204, the x-rays 210 can impact component atoms and impurities causing the x-ray fluorescent radiation 212 to emanate from the ceramic coating 204. Such fluorescent radiation 212 can be detected by the detector 208. Optionally, the detector 208 can be aligned at an angle $\theta$ relative to the plane of the surface 216 of the ceramic coating 204. The angle $\theta$ can be different from the angle $\alpha$ and its supplementary angle. For example, the angle $\theta$ can be greater than the critical angle. In particular, the angle $\theta$ can be in a range of 20° to 160° relative to the plane surface, such as a range of 45° to 135°, or even range of 75° to 105°.

It has been discovered that the distance the x-rays 210 will traverse a ceramic coating 204 toward the crystalline surface 214 can be at least 10 nm and is not limited by the wavelength of the x-rays 210. For example, the thickness can be at least 100 nm, such as at least 1 μm, or even at least 5 μm. In an example, the coating thickness is not greater than 1 mm.

In a particular example, the ceramic coating 204 is amorphous. In another example, the ceramic coating 204 is polycrystalline. The ceramic coating 204 can include alumina, yttria, aluminum nitride, amorphous silicon, polycrystalline silicon, zirconia, tantalum oxide, or any combination thereof. In general, the ceramic coating 204 may be x-ray transmissive. In an example, the ceramic coating 204 comprises is an alumina-based ceramic. In another example, the ceramic coating 204 is an aluminosilicate-based ceramic. For example, the ceramic coating 204 can be doped with a variety of dopants, such as yttrium or zirconium, or can include various impurities, such as iron, copper, and other transition metals. In particular example, the ceramic coating 204 includes yttria doped alumina.

Returning to FIG. 1, the characteristics of the detected electromagnetic radiation can be compared to a characteristic associated with impurities, as illustrated at 106. For example, a frequency, wavelength, or energy level of fluoresced electromagnetic radiation can be compared to expected values for various impurities. In general, the wavelength of the fluoresced electromagnetic radiation is in a range of 0.05 nm to 30 nm, such as a range of 0.05 nm to 5 nm. In particular, measured constituent atoms or measured impurities may fluoresce at a wavelength in the range of 0.05 nm to 0.9 nm. As such, the detected wavelength spectrum can be compared with the expected wavelength fluorescence values associated with constituent atoms and potential impurities to determine the presence of impurities or the quality of the formed ceramic coating 204.

Further, relative characteristics of the detected electromagnetic radiation can be compared between detected impurities and constituent atoms to determine composition and levels of impurity, as illustrated at 108 of FIG. 1. For example, a comparison of peak heights or counts between constituent atoms and impurities can be used to determine a relative composition.

Figure 3:
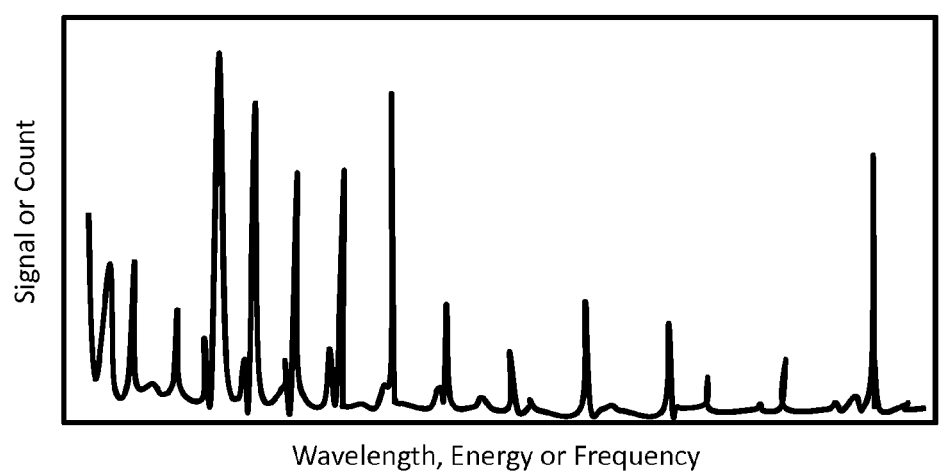
FIG. 3 includes a graph exemplifying detected electromagnetic radiation.

In a particular example, FIG. 3 illustrates a detection spectrum in which constituent atoms and impurities are detected based on energy level, wavelength, or frequency charted along the domain of the graph of FIG. 3. Relative counts indicated along the range of the chart can be compared to further determine composition of the impurities relative to the desired constituent atoms. In addition, the relative peak heights or counts can be used to differentiate constituents of the bulk material of the ceramic coating 204 from constituents of the crystalline surface 214 of the underlying crystalline substrate 202.

In a first aspect, a method of testing for impurities includes directing an x-ray source 206 toward a surface 216 at an angle α relative to the plane of the surface 216, the surface 216 defined by a ceramic coating 204 over a crystalline substrate 202; detecting x-ray fluorescent radiation 212 emitted from the ceramic coating 204 at an angle θ different from the angle α and its supplementary angle; and comparing characteristics of the detected x-ray fluorescent radiation 212 to characteristics associated with impurities.

In an example of the first aspect, the angle α is not greater than a critical angle. For example, the angle α is not greater than 15° relative to the plane of the surface 216, such as not greater than 10°. In an example, the angle α is in a range of 0.01° to 10°, such as a range of 0.015° to 5.0°, or a range of 1.0° to 5.0°.

In another example of the first aspect and the above examples, the angle θ is greater than the critical angle. For example, the angle θ is in a range of 20° to 160° relative to the plane of the surface 216, such as a range of 45° to 135°, or a range of 75° to 105°.

In a further example of the first aspect and the above examples, the x-rays 210 derived from the x-ray source 206 have a wavelength in the range of 0.01 nm to 10 nm, such as a range of 0.01 nm to 1 nm.

In an additional example of the first aspect and the above examples, the crystalline substrate 202 is a monocrystalline silicon substrate.

In another example of the first aspect and the above examples, the ceramic coating 204 is polycrystalline.

In a further example of the first aspect and the above examples, the ceramic coating 204 is amorphous.

In an additional example of the first aspect and the above examples, the ceramic coating 204 is x-ray transmissive.

In another example of the first aspect and the above examples, the ceramic coating 204 comprises alumina. For example, the ceramic coating 204 can include yttria doped alumina.

In a further example of the first aspect and the above examples, the impurity is a transition metal.

In an additional example of the first aspect and the above examples, the x-ray fluorescent radiation 212 has a wavelength in a range of 0.05 nm to 30 nm.

In another example of the first aspect and the above examples, the ceramic coating 204 has a thickness of at least 10 nm. For example, the thickness is at least 100 nm, such as at least 1 micron, or at least 5 microns. In an example, the thickness is not greater than 1 mm.

In a further example of the first aspect and the above examples, the characteristic includes wavelength, frequency, or energy.

In an additional example of the first aspect and the above examples, the method further includes determining a concentration of the impurity based on a relative characteristic of the detected x-ray fluorescent radiation 212. For example, the relative characteristic includes peak height or count associated with an impurity atom relative to the peak height or count of x-ray fluorescent radiation 212 associated with a constituent atom.

Note that not all of the activities described above in the general description or the examples are required, that a portion of a specific activity may not be required, and that one or more further activities may be performed in addition to those described. Still further, the order in which activities are listed are not necessarily the order in which they are performed.

In the foregoing specification, the concepts have been described with reference to specific embodiments. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of invention.

As used herein, the terms "comprises," "comprising," "includes," "including," "has," "having" or any other variation thereof, are intended to cover a non-exclusive inclusion. For example, a process, method, article, or apparatus that comprises a list of features is not necessarily limited only to those features but may include other features not expressly listed or inherent to such process, method, article, or apparatus. Further, unless expressly stated to the contrary, "or" refers to an inclusive-or and not to an exclusive-or. For example, a condition A or B is satisfied by any one of the following: A is true (or present) and B is false (or not present), A is false (or not present) and B is true (or present), and both A and B are true (or present).

Also, the use of "a" or "an" are employed to describe elements and components described herein. This is done merely for convenience and to give a general sense of the scope of the invention. This description should be read to include one or at least one and the singular also includes the plural unless it is obvious that it is meant otherwise.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

After reading the specification, skilled artisans will appreciate that certain features are, for clarity, described herein in the context of separate embodiments, may also be provided in combination in a single embodiment. Conversely, various features that are, for brevity, described in the context of a single embodiment, may also be provided separately or in any subcombination. Further, references to values stated in ranges include each and every value within that range.

What is claimed is:

1. A method of testing for impurities, the method comprising:
    directing x-rays from an x-ray source toward a surface at an angle α relative to a plane of the surface, the surface defined by a ceramic coating over a crystalline substrate;
    detecting x-ray fluorescent radiation emitted from the ceramic coating at an angle θ different from the angle α and its supplementary angle; and
    comparing characteristics of the detected x-ray fluorescent radiation to characteristics associated with impurities.

2. The method of claim 1, wherein the angle α is not greater than a critical angle.

3. The method of claim 1, wherein the angle α is in a range of 0.015° to 5.0°.

4. The method of claim 1, wherein the x-rays derived from the x-ray source have a wavelength in the range of 0.01 nm to 10 nm.

5. The method of claim 1, wherein the crystalline substrate is a monocrystalline silicon substrate.

6. The method of claim 1, wherein the ceramic coating is polycrystalline.

7. The method of claim 1, wherein the ceramic coating is amorphous.

8. The method of claim 1, wherein the ceramic coating comprises alumina.

9. The method of claim 8, wherein the ceramic coating comprising yttria doped alumina.

10. The method of claim 1, wherein the impurities comprise is a transition metal.

11. The method of claim 1, wherein the x-ray fluorescent radiation has a wavelength in a range of 0.05 nm to 30 nm.

12. The method of claim 1, wherein the ceramic coating has a thickness of at least 10 nm.

13. The method of claim 12, wherein the thickness is at least 100 nm.

14. The method of claim 13, wherein the thickness is at least 1 micron.

15. The method of claim 14, wherein the thickness is at least 5 microns.

16. The method of claim 12, wherein the thickness is not greater than 1 mm.

17. The method of claim 1, wherein the characteristics include wavelength, frequency, or energy.

18. The method of claim 1, further comprising determining a concentration of the impurities based on a relative characteristic of the detected x-ray fluorescent radiation.

19. The method of claim 18, wherein the relative characteristic includes peak height or count associated with an impurity atom relative to the peak height or count of x-ray fluorescent radiation associated with a constituent atom.

20. A method of testing for impurities, the method comprising:
    directing x-rays from an x-ray source toward a surface at an angle α relative to a plane of the surface, the surface defined by a ceramic coating over a crystalline substrate, x-rays from the x-ray source migrating through a bulk material of the ceramic coating to a surface of the crystalline substrate and reflecting from the surface of the crystalline substrate;
    detecting x-ray fluorescent radiation emitted from the bulk material of the ceramic coating at an angle θ different from the angle α and its supplementary angle; and
    comparing characteristics of the detected x-ray fluorescent radiation to characteristics associated with impurities.

* * * * *